(12) United States Patent
Childress (10) Patent No.: US 12,220,494 B2
(45) Date of Patent: Feb. 11, 2025

(54) ULTRAVIOLET LIGHT EMITTING DISINFECTING DEVICE

(71) Applicant: The Boeing Company, Chicago, IL (US)

(72) Inventor: Jamie J. Childress, Mercer Island, WA (US)

(73) Assignee: THE BOEING COMPANY, Arlington, VA (US)

( * ) Notice: Subject to any disclaimer, the term of this patent is extended or adjusted under 35 U.S.C. 154(b) by 794 days.

(21) Appl. No.: 17/366,476

(22) Filed: Jul. 2, 2021

(65) Prior Publication Data

US 2022/0111089 A1 Apr. 14, 2022

Related U.S. Application Data

(60) Provisional application No. 63/089,105, filed on Oct. 8, 2020.

(51) Int. Cl.
*A61L 2/10* (2006.01)
*B64D 47/02* (2006.01)
*B64F 5/30* (2017.01)

(52) U.S. Cl.
CPC ............... *A61L 2/10* (2013.01); *B64D 47/02* (2013.01); *B64F 5/30* (2017.01); *A61L 2202/11* (2013.01); *A61L 2202/14* (2013.01); *A61L 2202/25* (2013.01); *B64D 2203/00* (2013.01)

(58) Field of Classification Search
CPC ..... A61L 2/10; A61L 2202/11; A61L 2202/25; B64F 5/30
See application file for complete search history.

(56) References Cited

U.S. PATENT DOCUMENTS

| 2017/0112954 | A1 | 4/2017 | Dayton |
| 2017/0290935 | A1* | 10/2017 | Boodaghians ............ A47L 9/02 |
| 2020/0085984 | A1* | 3/2020 | Randers-Pehrson ...... A61L 2/10 |

FOREIGN PATENT DOCUMENTS

| WO | WO-2015012592 A1 * | 1/2015 | ............... A61L 2/10 |
| WO | 2019139743 A1 | 7/2019 | |

OTHER PUBLICATIONS

European Search Report; Application EP21199352; Mar. 4, 2022.

* cited by examiner

*Primary Examiner* — Sean E Conley
(74) *Attorney, Agent, or Firm* — MH2 TECHNOLOGY LAW GROUP LLP (57) ABSTRACT

Systems and methods are provided for disinfecting. One embodiment includes a disinfecting device. The disinfecting device includes a housing having an attachment surface and an illumination surface that are opposed along an axis, and a plurality of adjustable ultraviolet (UV) emitters disposed at the housing that have fields of illumination that are adjustable along multiple axes via rotational couplings to illuminate an enclosed space that the illumination surface faces.

20 Claims, 10 Drawing Sheets

ULTRAVIOLET LIGHT EMITTING DISINFECTING DEVICE

RELATED APPLICATIONS

This non-provisional patent application claims priority to U.S. Provisional Patent Application No. 63/089,105, filed on Oct. 8, 2020.

FIELD

The disclosure relates to the field of disinfection, and in particular, to disinfecting enclosed spaces such as the interior of an aircraft.

BACKGROUND

Enclosed spaces present a difficulty with respect to preventing infection, because the interior of an enclosed space is shared by all occupants of that enclosed space. Furthermore, many enclosed spaces, even those that are particularly small, such as aircraft or lavatories, receive a high volume of individuals throughout the day. Thus, a potential avenue for infection exists within enclosed spaces, in that infected individuals visiting an enclosed space may contaminate surfaces therein, and these contaminated surfaces become vectors by which other individuals who use the enclosed space can be infected.

Even when an effort is made to clean an enclosed space multiple times per day, the risk of infection can be non-trivial, especially for virulent diseases. Further compounding this issue, many surfaces which become contaminated throughout the day may not be in the direct line of sight of occupants, which reduces the likelihood of cleaning personnel disinfecting those surfaces.

Therefore, it would be desirable to have a method and apparatus that take into account at least some of the issues discussed above, as well as other possible issues.

SUMMARY

Embodiments described herein provide for disinfecting devices which retain Ultraviolet (UV) emitters that are capable of multi-axial rotation. In one embodiment, the UV emitters are separated from each other by a threshold distance. In such an embodiment, the UV emitters, by virtue of their distance from each other and ability to be adjusted to varied angles of orientation with respect to each other, have different fields of illumination that disinfect a variety of different portions of objects within an enclosed space. Thus, the disinfecting device illuminates more surfaces than could be accomplished via a single UV emitter. This increases the variety of surfaces bathed in disinfecting UV light, which increases the likelihood of fully decontaminating the enclosed space.

One embodiment is a system for disinfecting. The system includes a disinfecting device. The disinfecting device includes a housing having an attachment surface and an illumination surface that are opposed along an axis, and a plurality of adjustable ultraviolet (UV) emitters disposed at the housing that have fields of illumination that are adjustable along multiple axes via rotational couplings to illuminate an enclosed space that the illumination surface faces.

A further embodiment is an apparatus that includes a disinfecting device. The disinfecting device includes a housing, one or more embedded ultraviolet (UV) emitters that are configured to emit UV light out of the housing, and adjustable UV emitters that project from the housing, and are configured to emit UV light. The adjustable UV emitters include heads with rotational couplings that permit multi-axial rotation of the heads to alter fields of illumination.

A further embodiment is a method for disinfecting an enclosed space. The method includes attaching a disinfecting device having a plurality of adjustable UV emitters to a receiving surface of an enclosed space, providing for rotation of the adjustable UV emitters along multiple axes to enable each of the adjustable UV emitters to face a different portion of an object, and activating the disinfecting device to emit UV light from the adjustable UV emitters.

Other illustrative embodiments (e.g., methods and computer-readable media relating to the foregoing embodiments) may be described below. The features, functions, and advantages that have been discussed can be achieved independently in various embodiments or may be combined in yet other embodiments further details of which can be seen with reference to the following description and drawings.

DESCRIPTION OF THE DRAWINGS

Some embodiments of the present disclosure are now described, by way of example only, and with reference to the accompanying drawings. The same reference number represents the same element or the same type of element on all drawings.

DESCRIPTION

The figures and the following description provide specific illustrative embodiments of the disclosure. It will thus be appreciated that those skilled in the art will be able to devise various arrangements that, although not explicitly described or shown herein, embody the principles of the disclosure and are included within the scope of the disclosure. Furthermore, any examples described herein are intended to aid in understanding the principles of the disclosure, and are to be construed as being without limitation to such specifically recited examples and conditions. As a result, the disclosure is not limited to the specific embodiments or examples described below, but by the claims and their equivalents.

Figure 1A:
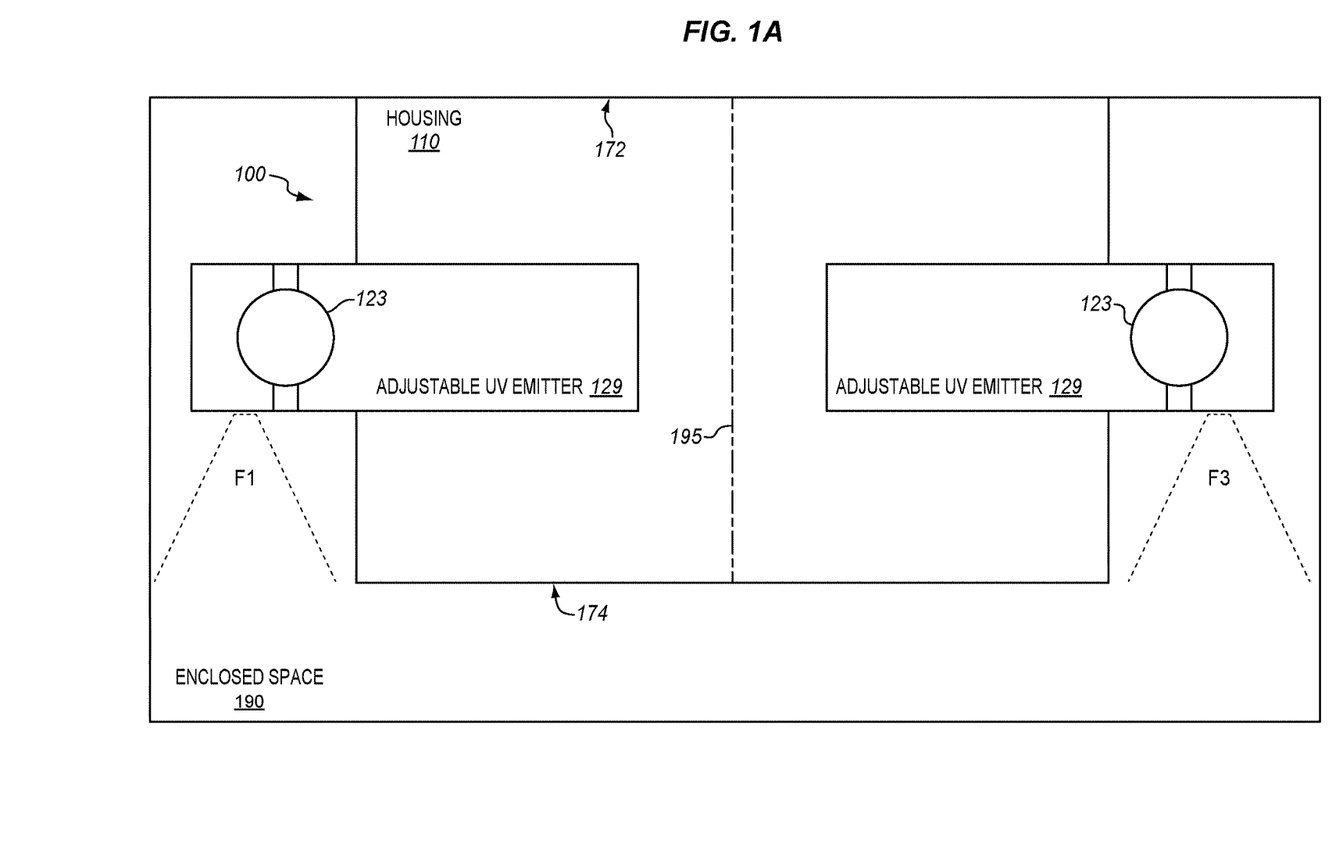
FIG. 1A is a block diagram of a disinfecting device in an illustrative embodiment.

FIG. 1A is a block diagram of a disinfecting device 100 in an illustrative embodiment. The disinfecting device 100 is disposed within an enclosed space 190. The enclosed space 190 comprises a volume of space that is surrounded, either fully or partially, by boundaries that restrict airflow. Hence, the enclosed space 190 may comprise a tent, a room in a building, a cabin of an aircraft, etc. The disinfecting device 100 comprises any suitable system, device, or component capable of performing disinfection by emitting ultraviolet (UV) light from multiple adjustable UV emitters 129.

The adjustable UV emitters 129 are disposed at a housing 110 of the disinfecting device 100. The housing 110 comprises a frame, support, or other mechanical components that physically retains the adjustable UV emitters 129 in desired positions at the disinfecting device 100. In this embodiment, the housing 110 defines an attachment surface 172, and an illumination surface 174, which are opposed along an axis 195 (e.g., a center line) of the housing 110. The attachment surface 172 is configured for attaching the housing 110 to a surface of the enclosed space. Meanwhile, the illumination surface 174 comprises a surface that faces outward towards the enclosed space 190 that will be disinfected by the adjustable UV emitters 129.

The adjustable UV emitters 129 emit UV light for purposes of disinfection. The UV light is absorbed by surfaces at the enclosed space 190 that are within fields of illumination (F1, F3) of the adjustable UV emitters 129. The UV light deactivates genetic material within viruses and/or bacteria disposed at the surfaces, rendering them inert. The fields of illumination F1 and F3 face outward from the illumination surface 174. That is, the fields of illumination F1 and F3 face generally in the direction defined by traveling the axis 195 from the attachment surface 172 to the illumination surface 174.

The adjustable UV emitters 129 each include a rotational coupling 123. The rotational coupling 123 comprises a physical component which enables adjustment of a field of illumination, by rotating a portion of a corresponding adjustable UV emitter 129.

Figure 1B:
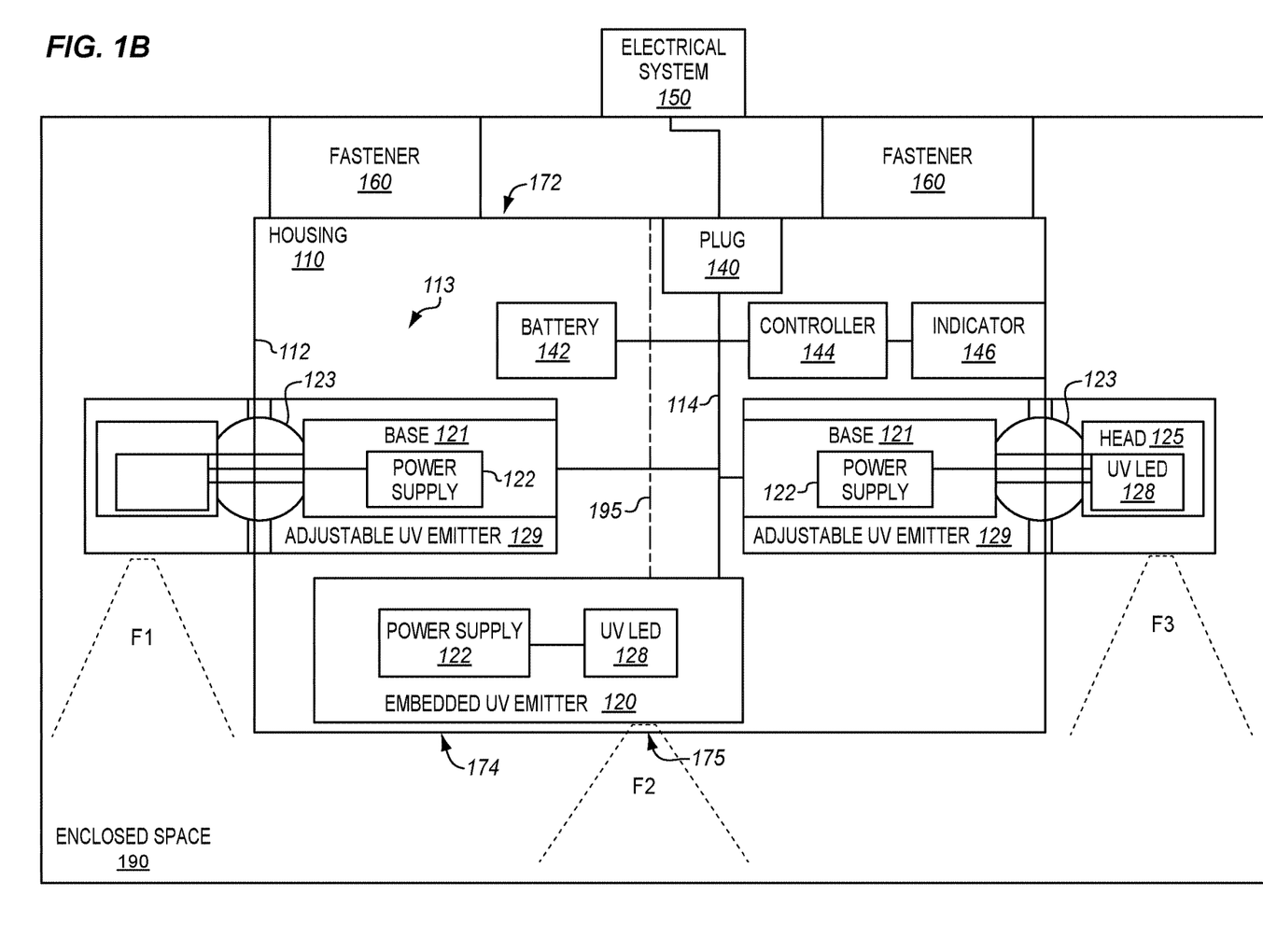
FIG. 1B is a further block diagram of a disinfecting device in an illustrative embodiment.

FIG. 1B is a further block diagram of a disinfecting device 100 in an illustrative embodiment. FIG. 1B depicts further components of a disinfecting device 100 of FIG. 1A in one embodiment. In this embodiment, one or more of the adjustable UV emitters 129 are at least partially disposed within a volume 113 defined by the housing 110. Furthermore, in this embodiment, the adjustable UV emitters 129 include heads 125 that are rotatable along multiple axes via the rotational couplings 123. The heads 125 each comprise a component that retains a UV Light Emitting Diode (LED) 128. By emitting UV light via a UV LED 128, a field of illumination is illuminated with UV light, resulting in disinfection. By adjusting angles of the heads 125, the fields of illumination (F1, F3) of the disinfecting device 100 are altered. This means that the disinfecting device 100 is capable of being adjusted to illuminate the interiors of enclosed spaces of varying sizes and shapes.

In this embodiment, the head 125 of each adjustable UV emitter 129 is coupled with a base 121 via the rotational coupling 123. The base 121 comprises a frame or support which stores a power supply 122 and/or facilitates affixation of the adjustable UV emitter 129 to the housing 110. The power supply 122 converts incoming electricity to a desired amount of voltage for the UV LED 128. The power supply 122 is electrically coupled with the UV LED 128 in the head 125.

In this embodiment, the disinfecting device 100 further includes one or more embedded UV emitters 120 disposed at the housing 110. The embedded UV emitter 120 may comprise an another one of adjustable UV emitters 129. However, in this embodiment, the embedded UV emitter includes a power supply 122 and UV LED 128, and is not adjustable. In one embodiment, the illumination surface 174 of the disinfecting device 100 includes a gap 175 that is aligned with the UV LED 128 of the embedded UV emitter 120.

In this embodiment, wiring 114 couples the embedded UV emitter 120 and adjustable UV emitters 129 with a power source such as a plug 140 and/or a battery 142. The plug 140 is coupled with an electrical system 150 (e.g., via an outlet) at an enclosed space, and the battery 142 stores energy for operating the UV LEDs 128. In this manner, the battery 142 may operate as a backup power supply if power from an electrical system 150 is interrupted. The battery 142 itself is retained within the housing 110.

Wiring 114 also supplies power to a controller 144 and indicator 146 (e.g., a small red LED) disposed within the housing 110. Controller 144 dictates the operations of the disinfecting device 100. In one embodiment, the controller 144 includes logic for switching to the battery 142 when power is interrupted at plug 140. In a further embodiment the controller 144 reports a low battery state by monitoring the battery 142 and lighting the indicator 146 if an amount of energy stored in the battery is below a threshold level (e.g., twenty percent). In a further embodiment, the controller 144 activates the embedded UV emitter 120 and adjustable UV emitters 129 for a limited time period in response to receiving input from a user (e.g., the pressing of an "on" button at the controller 144). This ensures that disinfection continues for a desired period of time (e.g., during a flight of an aircraft), while also ensuring that the disinfecting device 100 is turned off and battery power is not wasted after that period of time has elapsed (e.g., after a flight has been completed). In one embodiment, controller 144 is implemented as custom circuitry, as a hardware processor executing programmed instructions stored in memory, or some combination thereof.

Figure 2:
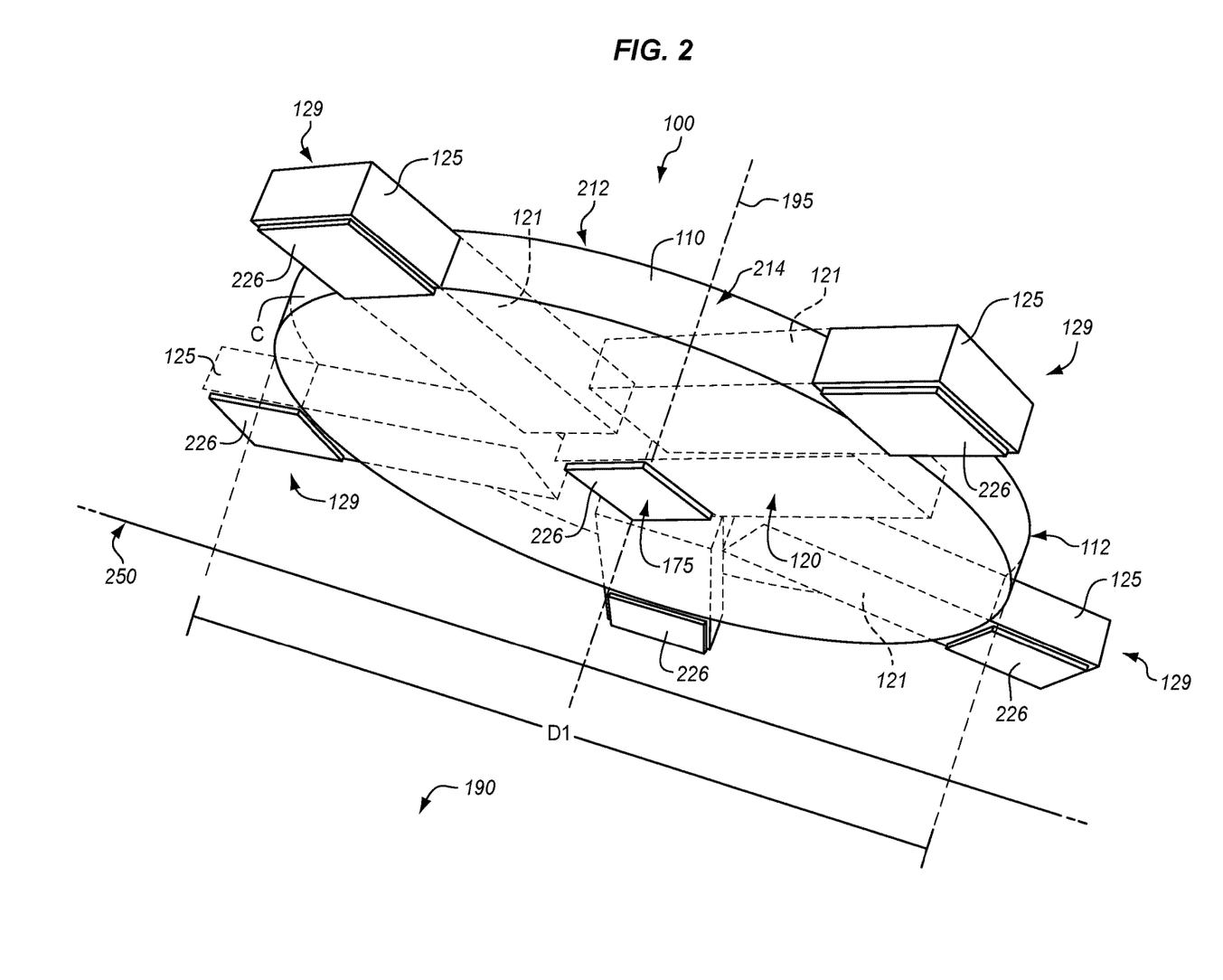
FIGS. 2-3 are perspective views of a disinfecting device in an illustrative embodiment.
Figure 3:
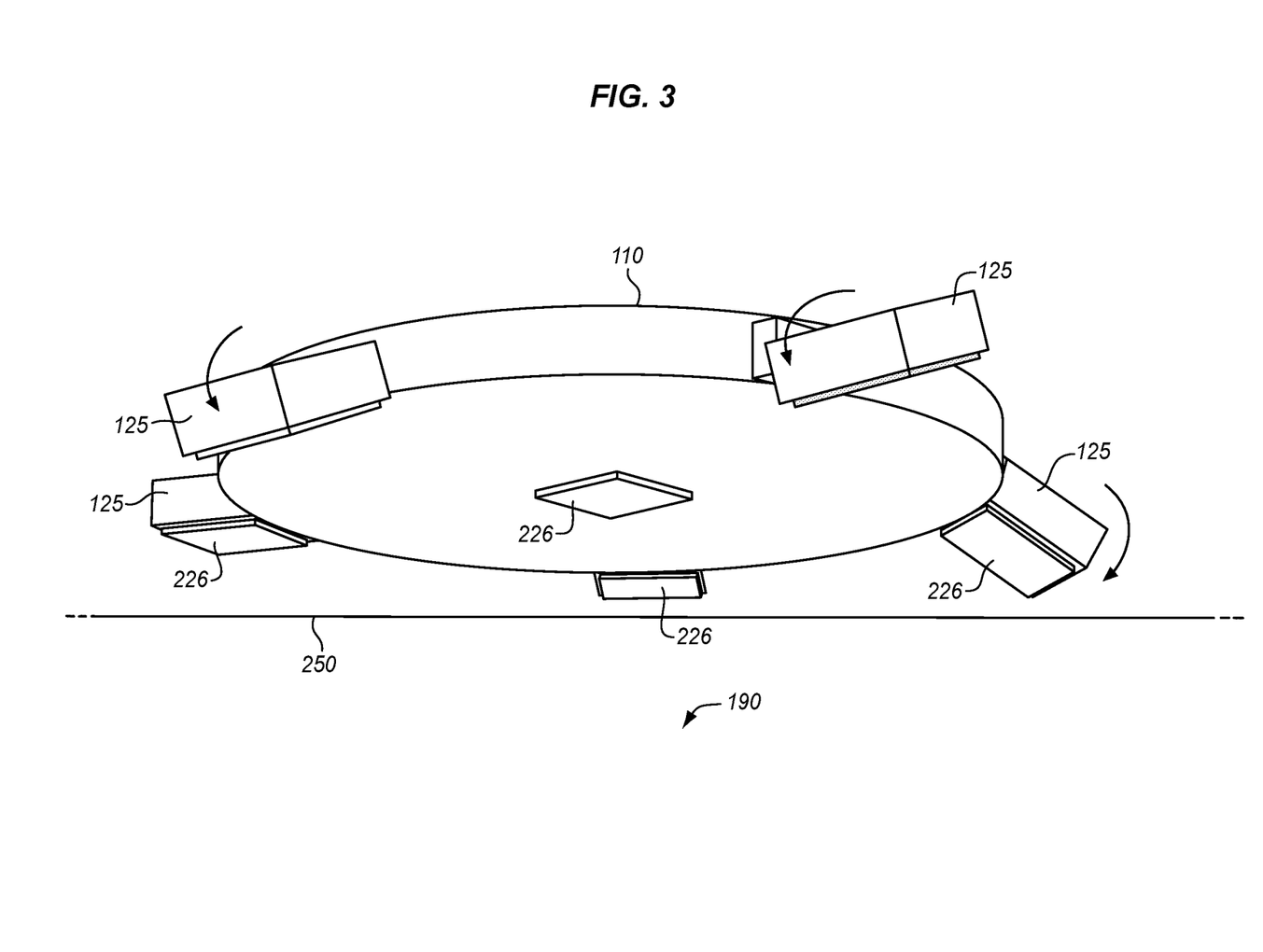

FIGS. 2-3 depict perspective views of the disinfecting device 100 in an illustrative embodiment. In this embodiment, the disinfecting device 100 has a cylindrical shape defined by walls 112 of a rigid material 214. The cylindrical shape has an axis 195 corresponding with its centerline, a diameter D1, and a circumference C. Housing 110 is disposed at a receiving surface 250, which may comprise a boundary (e.g., a ceiling, wall, panel, etc.) of an enclosed space 190 or an object within the enclosed space 190. In this embodiment, optical faces 226 (e.g., panels of UV-transparent material) are also depicted. Optical faces 226 physically protect UV LEDs 128 from being damaged by physical contact, such as an impact.

In this particular embodiment, one or more embedded UV emitters 120 are disposed entirely within the housing 110 such that the optical face 226 of each embedded UV emitter 120 is visible and aligned with a gap 175 at the illumination surface 174, but the rest of the embedded UV emitter 120 may be obscured. Adjustable UV emitters 129 are arranged around the periphery 212 of the housing 110 (e.g., radially, forming a polar array around the periphery 212). Any suitable number of embedded UV emitters 120 and adjustable UV emitters 129 may be utilized within the disinfecting device 100, as a matter of design choice.

In this embodiment, the adjustable UV emitters 129 are partially disposed within the housing 110 while their heads 125 project outward from the housing 110. This enables the heads 125 to be freely rotated along multiple axes in order to emit UV light in desired directions. Specifically, in this embodiment the bases 121 of the adjustable UV emitters 129 are at least partially enclosed within the housing 110, while heads 125 and optical faces 226 of the adjustable UV emitters 129 are external to the housing 110. This facilitates rotation of the heads 125 independent of the housing 110.

The UV LEDs 128 of the embedded UV emitter 120 and the adjustable UV emitters 129 emit UV light via optical faces 226. In one embodiment, UV LEDs 128 emit UV light at a wavelength of two hundred and twenty two nanometers, which is safe for humans. In such an environment, the embedded UV emitter 120 and adjustable UV emitters 129 may continue to emit UV light even while the enclosed space 190 is occupied.

As shown in FIG. 3, heads 125 of the adjustable UV emitters 129 are adjustable along multiple axes, and are capable of being rotated to various angles in order to emit UV light in different directions. This enables the heads 125 of the disinfecting device 100 to disinfect differing portions of the surface areas of objects within an enclosed space 190.

Figure 4:
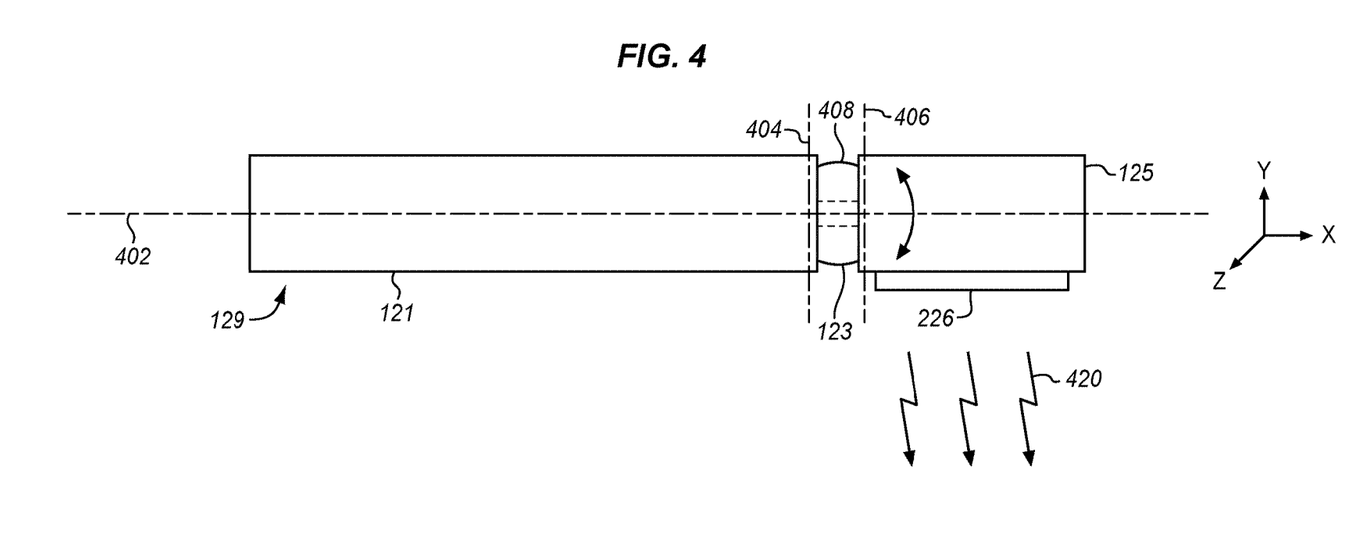
FIGS. 4-6 depict a UV emitter with a head that is adjustable in an illustrative embodiment.
Figure 5:
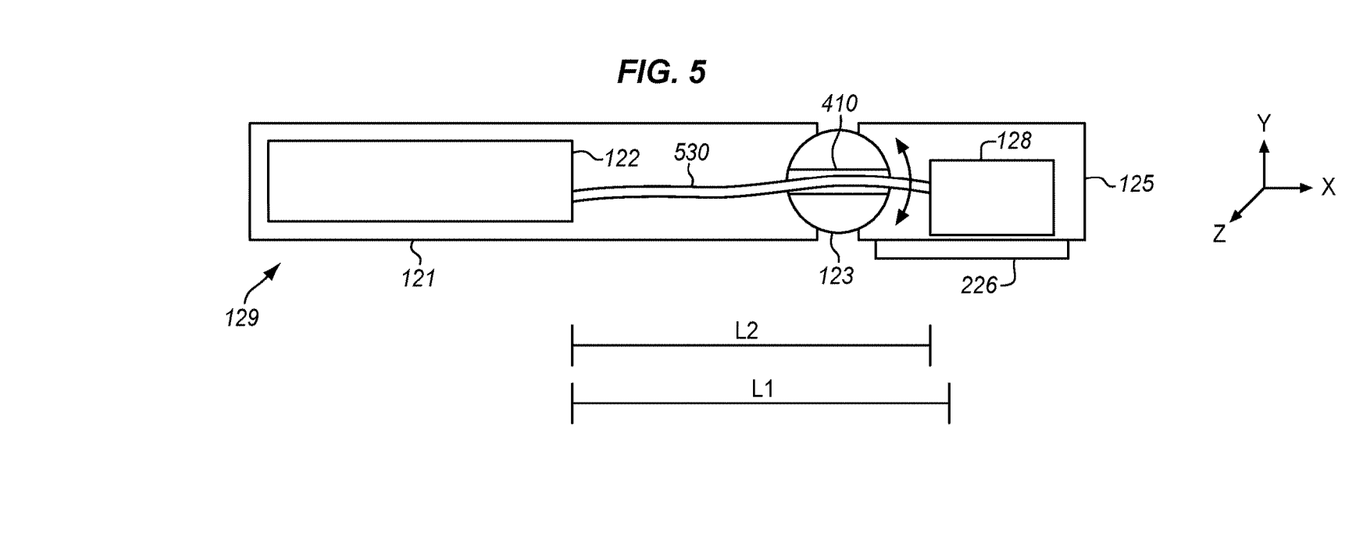
Figure 6:
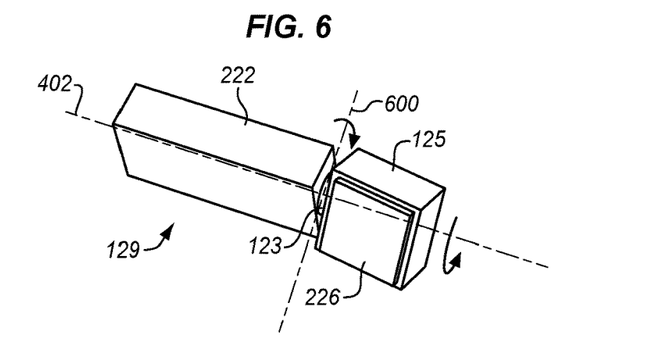

FIGS. 4-6 depict an adjustable UV emitter 129 that may be integrated into a disinfecting device 100 in an illustrative embodiment. As shown in FIG. 4, the base 121 of an adjustable UV emitter 129 is coupled with a head 125 via a rotational coupling 123 (e.g., comprising a ball joint 408, a universal joint, etc.). The optical face 226 emits UV light 420. The rotational coupling 123 enables rotation of the head 125 relative to the base 121 along multiple axes (e.g., along X, Y, and/or Z or some subset thereof, along a axis 402 of the base 121, along axis 404 and/or axis 406, etc.). In one embodiment, the rotational coupling 123 is tightly coupled against head 125 and base 121. Thus, a greater amount of force than the weight of head 125 or base 121 is necessary to overcome friction between head 125, base 121, and/or rotational coupling 123 in order to reorient the rotational coupling 123. This prevents the head 125 from sagging or otherwise changing position after it has been rotated to a desired angle via the rotational coupling 123.

FIG. 5 is a section cut view of the adjustable UV emitter 129, and illustrates that base 121 houses a power supply 122, which converts received electrical energy to a desired voltage (e.g., twenty-four volts) and/or amperage for use by a Light Emitting Diode (LED) 128. FIG. 5 further illustrates wiring 530 that electrically connects power supply 122 to LED 128. Wiring 530 reaches the LED 128 via passage 410 in rotational coupling 123. That is, for each of the adjustable UV emitters 129, the rotational coupling 123 defines a passage 410 that houses wiring 530 coupling an LED 128 of the adjustable UV emitter 129 to a power supply 122 of the adjustable UV emitter 129. This arrangement eliminates the need for the UV emitters 129 to keep power supplies within their heads 125.

The length L1 of wiring 530 when held taut exceeds a length L2 corresponding to a distance between the LED 128 and the power supply 122. This excess length enables the wiring 530 to move to accommodate repositioning of the rotational coupling 123, without being pinched or placed into tension.

FIG. 6 provides a perspective view wherein a head 125 of a adjustable UV emitter 129 has been adjusted to a new position via rotational coupling 123. As shown in FIG. 6, the head 125 of the adjustable UV emitter 129 has been rotated about axis 402 of the body, as well as axis 600.

Figure 7:
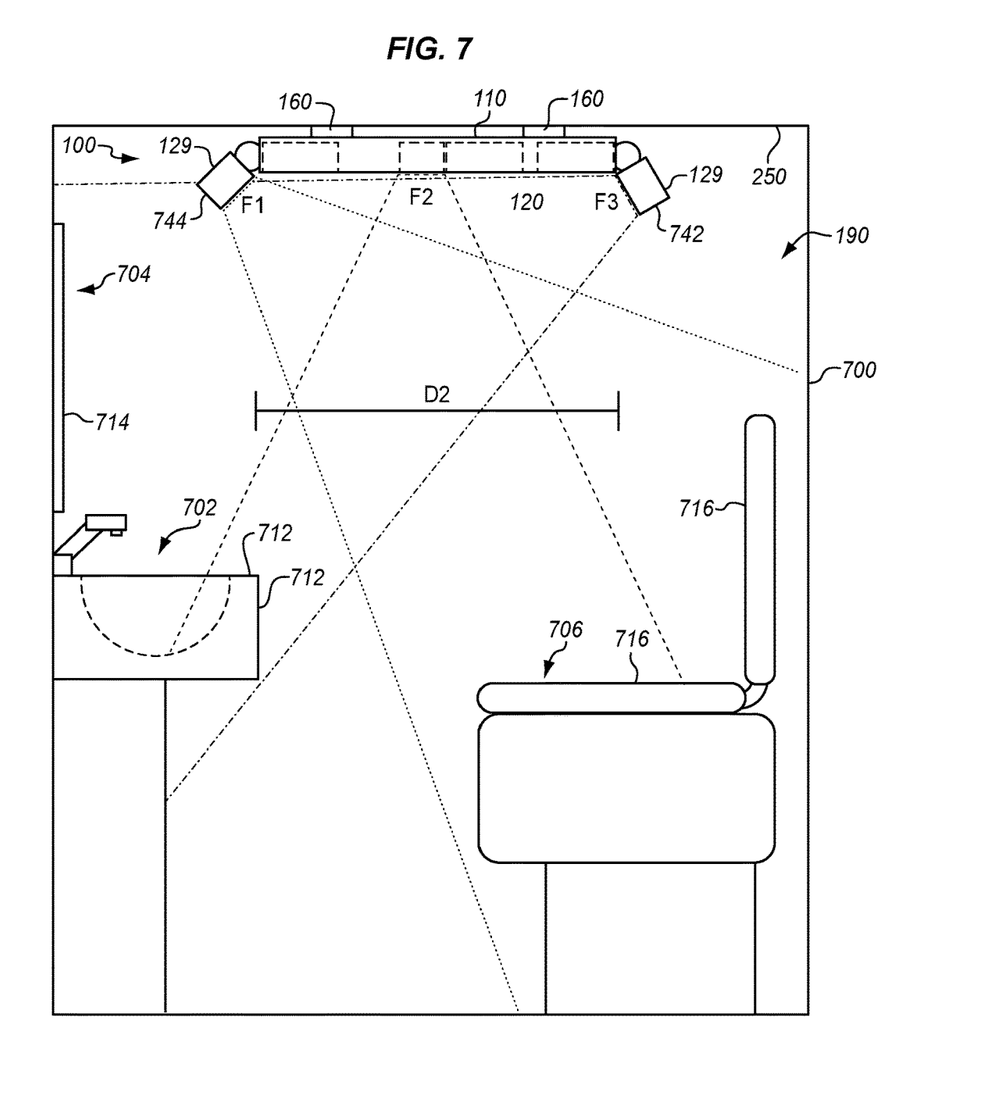
FIG. 7 depicts a disinfecting device located within a lavatory in an illustrative embodiment.
Figure 8:
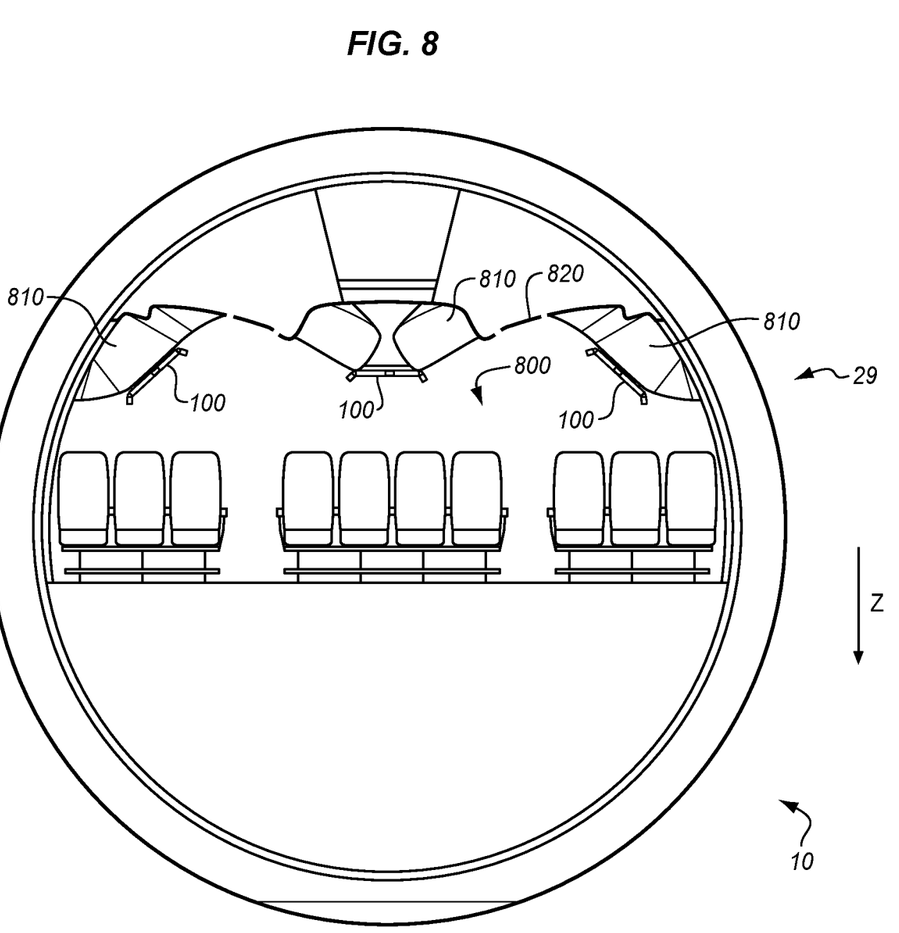
FIG. 8 depicts disinfecting devices located within a cabin of an aircraft in an illustrative embodiment.

While the above FIGS. discuss the composition of a disinfecting device 100 and UV emitters within a disinfecting device 100, the following FIGS. 7-8 depict placement and alignment of disinfecting devices 100 in order to facilitate disinfection of surfaces in illustrative embodiments.

FIG. 7 depicts a disinfecting device 100 located within a lavatory 700 of an aircraft 10 in an illustrative embodiment. In this embodiment, the disinfecting device 100 is located within an enclosed space 190 defined by the lavatory 700. The disinfecting device 100 is installed onto a receiving surface 250 via fasteners 160. Fasteners 160 may comprise glue, double-sided tape, receptacles for screws or bolts, etc. In this manner, the fasteners 160 facilitate installation of the disinfecting device onto the receiving surface 250.

The enclosed space 190 includes multiple objects 702, 704, and 706 having surfaces 712, 714, and 716 respectively. Heads 125 of the adjustable UV emitters 129 of the disinfecting device 100 are arranged around a periphery 212 of the disinfecting device 100, such that heads 125 on opposite ends of the disinfecting device 100 are separated by a distance D2 (e.g., between eight and twenty inches). In one embodiment, the distance D2 between the heads 125 of the adjustable UV emitters 129 that are disposed on opposite sides of the disinfecting device 100 is at least equal to a diameter D1 of the housing 110 of the disinfecting device 100. That is, the adjustable UV emitters 129 are distributed radially along the circumference of the disinfecting device 100.

The separation distance, combined with the ability to adjust the heads 125 to orientations 742 and 744 that are unique relative to the orientations of other heads 125 at the disinfecting device, enables the heads 125 to emit UV light that directly illuminates the surfaces 712, 714, and 716 from different fields of illumination F1, F2, and F3, even though the surfaces 712, 714, and 716 are disposed at different locations and face in different directions. Phrased another way, each head 125 directly illuminates a different combination of surfaces and/or portions of the objects 702, 704, and 706. Because UV light does not reflect but rather is absorbed by most surfaces, direct illumination of the surfaces 712, 714, and 716 via the heads 125 is highly desirable. This ability to disinfect all of the surfaces 712, 714, and 716 is not possible from any point source of UV light. Thus, disinfecting device 100 provides a technical benefit by enabling a greater amount of surfaces, arranged at a greater amount of angles, to be disinfected via the installation of a single disinfecting device.

FIG. 8 depicts multiple disinfecting devices 100 located within a cabin 800 of an aircraft in an illustrative embodiment. In this embodiment, the disinfecting devices 100 are affixed/installed at a ceiling 820 of the aircraft, proximate to stow bins 810. The disinfecting devices 100 may be activated in between flights to disinfect surfaces at the cabin 800. In one embodiment wherein the disinfecting devices 100 emit UV light having a wavelength of two hundred and twenty two nanometers, the disinfecting devices 100 have no deleterious effects on passengers, and are left on for the duration of a flight to minimize the risk of infection.

Illustrative details of the operation of disinfecting device 100 will be discussed with regard to FIG. 9. Assume, for this embodiment, that an aircraft awaits installation of one or more disinfecting devices 100 in order to facilitate cleaning of the aircraft during an ongoing health crisis that proceeds for a period of multiple days.

Figure 9:
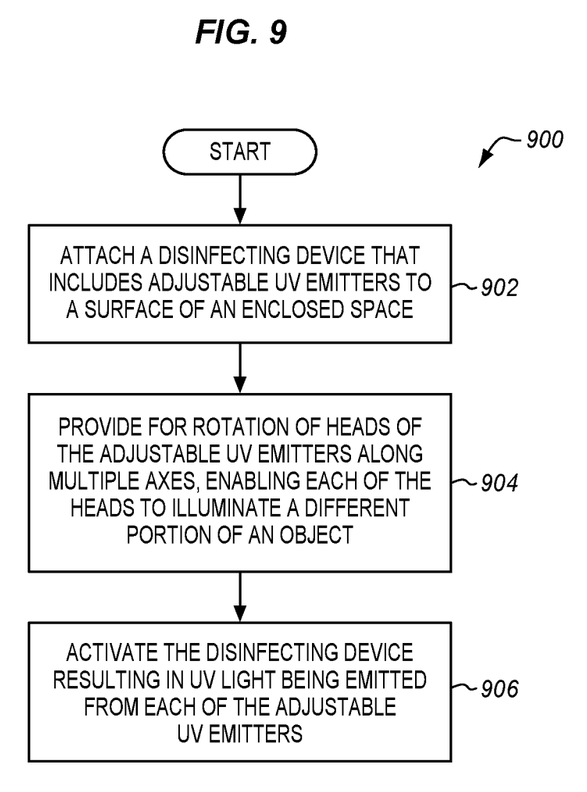
FIG. 9 is a flowchart illustrating a method for disinfecting an enclosed space in an illustrative embodiment.

FIG. 9 is a flowchart illustrating a method 900 for disinfecting an enclosed space in an illustrative embodiment. The steps of method 900 are described with reference to disinfecting device 100 of FIG. 1, but those skilled in the art will appreciate that method 900 may be performed in other systems and/or devices. The steps of the flowcharts described herein are not all inclusive and may include other steps not shown. The steps described herein may also be performed in an alternative order.

Method 900 includes attaching 902 a disinfecting device 100 that includes adjustable UV emitters 129 to a receiving surface 250 of an enclosed space 190. In one embodiment, attaching 902 comprises placing fasteners 160 in the form of double-sided tape onto the disinfecting device 100, and pressing the disinfecting device 100 into the receiving surface 250 of the enclosed space 190. In a further embodiment, attaching 902 comprises driving fasteners 160 in the form of screws or bolts through disinfecting device 100 and into the receiving surface 250. In a further embodiment, attaching 902 the disinfecting device 100 comprises coupling the disinfecting device 100 with an electrical system (e.g., electrical system 1126) of an aircraft (e.g., aircraft 1102). After attachment, a technician may identify an object 702 in the enclosed space 190 for which disinfection is desired. In one embodiment, the object 702 includes surfaces 712 that have the potential to become contaminated via human use of the enclosed space 190 (e.g., a sink, toilet, or mirror of a lavatory).

Method 900 further includes providing 904 for rotation of the heads 125 of the adjustable UV emitters 129 along multiple axes, enabling each of the heads 125 to face a different portion of the object 702 (e.g., a different one of surfaces 712). In one embodiment, rotating the heads 125 comprises manipulating the ball joints 408 of the adjustable UV emitters 129. Rotating the heads 125 to illuminate the object 702 from different angles beneficially increases an amount of surface area at surfaces 712 of object 702 that are exposed to disinfecting UV light.

Method 900 further includes activating 906 the disinfecting device 100, resulting in UV light being emitted from each of the adjustable UV emitters 129. In one embodiment, the UV light that is emitted from the heads has a wavelength of two hundred and twenty two nanometers, which destroys bacteria and viruses without being detrimental to human health.

Method 900 provides a technical benefit by enabling a single installed disinfecting device to illuminate objects from a variety of different fields of illumination, thereby increasing an overall surface area of an enclosed space being disinfected from a single installed device.

Examples

In the following examples, additional processes, systems, and methods are described in the context of a disinfecting device for an enclosed space.

Figure 10:
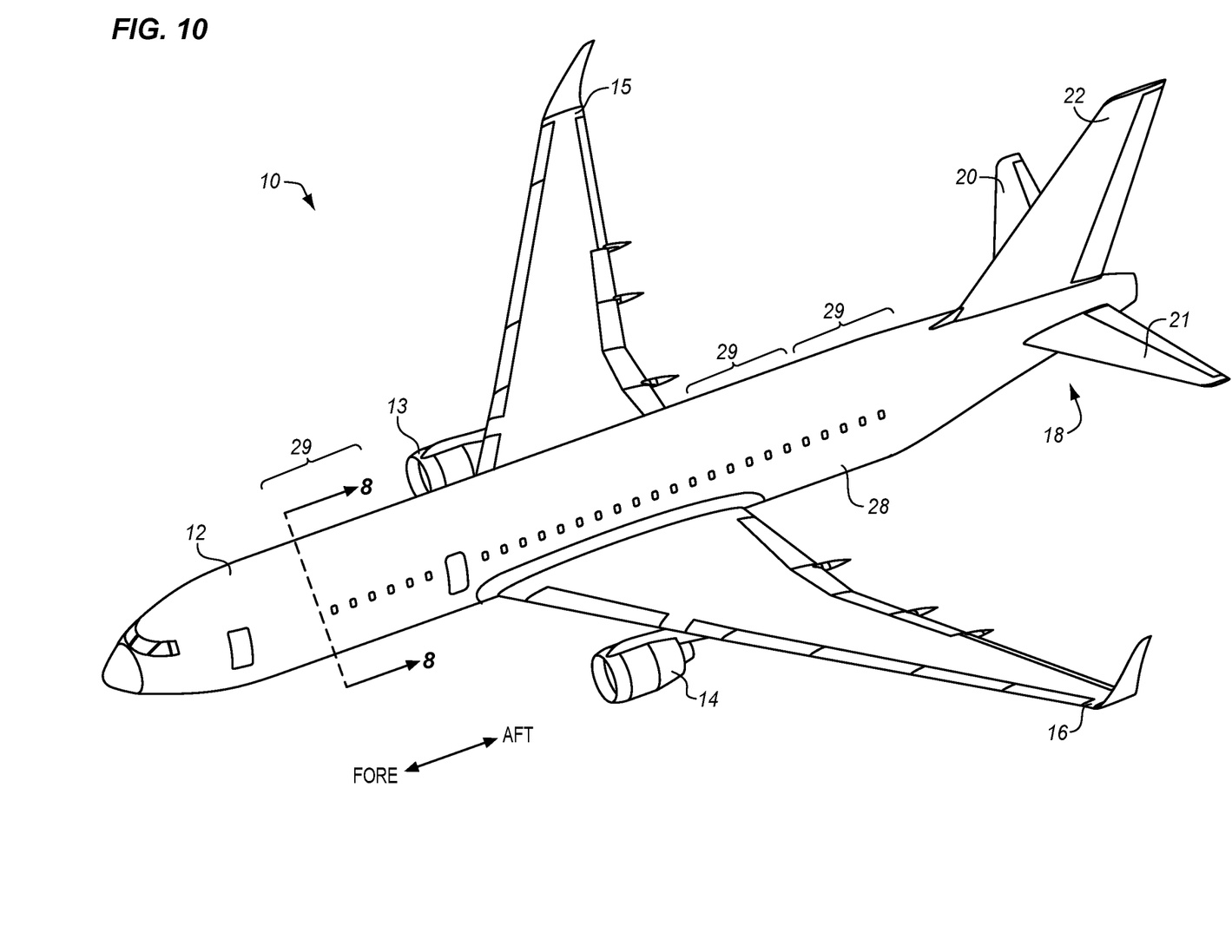
FIG. 10 illustrates an aircraft in an illustrative embodiment.

Turning now to FIG. 10, an illustration of an aircraft 10 is depicted for which the systems and methods described herein may be implemented. In this illustrative example, aircraft 10 includes wing 15 and wing 16 attached to fuselage 28 having a nose 12. Aircraft 10 includes engine 13 attached to wing 15 and engine 14 attached to wing 16. Tail section 18 is also attached to fuselage 28. Horizontal stabilizer 20, horizontal stabilizer 21, and vertical stabilizer 22 are attached to tail section 18 of fuselage 28. The fuselage 28 itself is formed from multiple barrel sections 29 which have been joined together. In this embodiment, three barrel sections 29 are labeled, but any suitable number of barrel sections 29 may be utilized to form the fuselage 28 as a matter of design choice. Disinfecting devices 100 may be placed at any suitable locations within the aircraft 10 for which disinfection is desired.

Figure 11:
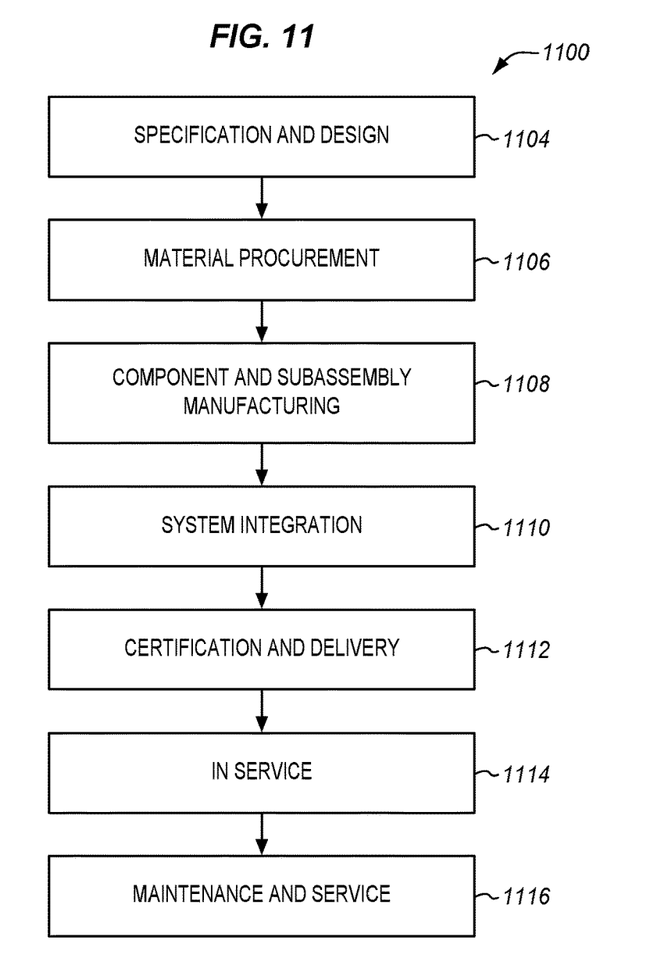
FIG. 11 is a flow diagram of aircraft production and service methodology in an illustrative embodiment.
Figure 12:
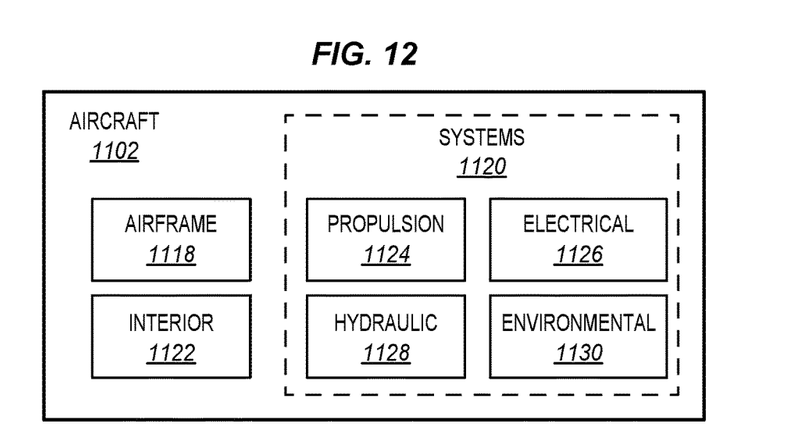
FIG. 12 is a block diagram of an aircraft in an illustrative embodiment.

Referring more particularly to the drawings, embodiments of the disclosure may be described in the context of aircraft manufacturing and service in method 1100 as shown in FIG. 11 and an aircraft 1102 as shown in FIG. 12. During pre-production, method 1100 may include specification and design 1104 of the aircraft 1102 and material procurement 1106. During production, component and subassembly manufacturing 1108 and system integration 1110 of the aircraft 1102 takes place. Thereafter, the aircraft 1102 may go through certification and delivery 1112 in order to be placed in service 1114. While in service by a customer, the aircraft 1102 is scheduled for routine work in maintenance and service 1116 (which may also include modification, reconfiguration, refurbishment, and so on). Apparatus and methods embodied herein may be employed during any one or more suitable stages of the production and service described in method 1100 (e.g., specification and design 1104, material procurement 1106, component and subassembly manufacturing 1108, system integration 1110, certification and delivery 1112, service 1114, maintenance and service 1116) and/or any suitable component of aircraft 1102 (e.g., airframe 1118, systems 1120, interior 1122, propulsion system 1124, electrical system 1126, hydraulic system 1128, environmental system 1130).

Each of the processes of method 1100 may be performed or carried out by a system integrator, a third party, and/or an operator (e.g., a customer). For the purposes of this description, a system integrator may include without limitation any number of aircraft manufacturers and major-system subcontractors; a third party may include without limitation any number of vendors, subcontractors, and suppliers; and an operator may be an airline, leasing company, military entity, service organization, and so on.

As shown in FIG. 12, the aircraft 1102 produced by method 1100 may include an airframe 1118 with a plurality of systems 1120 and an interior 1122. Examples of systems 1120 include one or more of a propulsion system 1124, an electrical system 1126, a hydraulic system 1128, and an environmental system 1130. Any number of other systems may be included. Although an aerospace example is shown, the principles of the invention may be applied to other industries, such as the automotive industry.

As already mentioned above, apparatus and methods embodied herein may be employed during any one or more of the stages of the production and service described in method 1100. For example, components or subassemblies corresponding to component and subassembly manufacturing 1108 may be fabricated or manufactured in a manner similar to components or subassemblies produced while the aircraft 1102 is in service. Also, one or more apparatus embodiments, method embodiments, or a combination thereof may be utilized during the subassembly manufacturing 1108 and system integration 1110, for example, by substantially expediting assembly of or reducing the cost of an aircraft 1102. Similarly, one or more of apparatus embodiments, method embodiments, or a combination thereof may be utilized while the aircraft 1102 is in service, for example and without limitation during the maintenance and service 1116. Thus, the invention may be used in any stages discussed herein, or any combination thereof, such as specification and design 1104, material procurement 1106, component and subassembly manufacturing 1108, system integration 1110, certification and delivery 1112, service 1114, maintenance and service 1116 and/or any suitable component of aircraft 1102 (e.g., airframe 1118, systems 1120, interior 1122, propulsion system 1124, electrical system 1126, hydraulic system 1128, and/or environmental system 1130).

In one embodiment, a part comprises a portion of airframe 1118, and is manufactured during component and subassembly manufacturing 1108. The part may then be assembled into an aircraft in system integration 1110, and then be utilized in service 1114 until wear renders the part unusable.

Then, in maintenance and service 1116, the part may be discarded and replaced with a newly manufactured part. Inventive components and methods may be utilized throughout component and subassembly manufacturing 1108 in order to manufacture new parts.

Any of the various control elements (e.g., electrical or electronic components) shown in the figures or described herein may be implemented as hardware, a processor implementing software, a processor implementing firmware, or some combination of these. For example, an element may be implemented as dedicated hardware. Dedicated hardware elements may be referred to as "processors", "controllers", or some similar terminology. When provided by a processor, the functions may be provided by a single dedicated processor, by a single shared processor, or by a plurality of individual processors, some of which may be shared. Moreover, explicit use of the term "processor" or "controller" should not be construed to refer exclusively to hardware capable of executing software, and may implicitly include, without limitation, digital signal processor (DSP) hardware, a network processor, application specific integrated circuit (ASIC) or other circuitry, field programmable gate array (FPGA), read only memory (ROM) for storing software, random access memory (RAM), non-volatile storage, logic, or some other physical hardware component or module.

Also, a control element may be implemented as instructions executable by a processor or a computer to perform the functions of the element. Some examples of instructions are software, program code, and firmware. The instructions are operational when executed by the processor to direct the processor to perform the functions of the element. The instructions may be stored on storage devices that are readable by the processor. Some examples of the storage devices are digital or solid-state memories, magnetic storage media such as a magnetic disks and magnetic tapes, hard drives, or optically readable digital data storage media.

Although specific embodiments are described herein, the scope of the disclosure is not limited to those specific embodiments. The scope of the disclosure is defined by the following claims and any equivalents thereof.

What is claimed is:

1. A system for disinfecting, the system comprising:
a disinfecting device comprising:
a housing having an attachment surface and an illumination surface that are opposed along an axis, wherein the housing is a cylinder with the attachment surface at one end of the cylinder and the illumination surface at the opposite end of the cylinder; and
a plurality of adjustable ultraviolet (UV) emitters disposed at the housing that have fields of illumination that are adjustable along multiple axes via rotational couplings to illuminate an enclosed space that the illumination surface faces, wherein each adjustable UV emitter comprises a base coupled with a head via a corresponding rotational coupling, and wherein the base of each UV emitter comprises a power supply for said each UV emitter.

2. The system of claim 1 wherein:
the adjustable UV emitters are arranged radially along a circumference of the housing, and
the head of each of the adjustable UV emitters projects outward from the housing, wherein the head retains a Light Emitting Diode (LED), and the head is configured for reorientation via one of the rotational couplings to alter a field of illumination.

3. The system of claim 1 wherein:
the adjustable UV emitters emit UV light at a wavelength of (222) nanometers.

4. The system of claim 1 wherein:
the rotational couplings comprise ball joints.

5. The system of claim 1 wherein:
for each adjustable UV emitter of the plurality, the rotational coupling defines a passage that houses wiring coupling a Light Emitting Diode (LED) of the UV emitter to a power supply of the adjustable UV emitter.

6. The system of claim 1 further comprising:
a battery disposed within the housing that provides power to the disinfecting device.

7. The system of claim 1 further comprising:
fasteners that facilitate installation of the disinfecting device onto a receiving surface.

8. The system of claim 1 wherein:
the enclosed space comprises a portion of an aircraft, and the disinfecting device is affixed to the aircraft.

9. An apparatus comprising a disinfecting device, the disinfecting device comprising:
a housing, wherein the housing is a cylinder;
one or more embedded ultraviolet (UV) emitters that are configured to emit UV light out of the housing; and
adjustable UV emitters that project from the housing, and are configured to emit UV light,
wherein each adjustable UV emitter comprises a base coupled with a head via a corresponding rotational coupling,
wherein the base of each adjustable UV emitter comprises a power supply for said each UV emitter,
and wherein the adjustable UV emitters include rotational couplings that permit multi-axial rotation of the heads to alter fields of illumination.

10. The apparatus of claim 9 wherein:
the embedded UV emitters each include a UV Light Emitting Diode (LED) aligned with a gap at the housing,
the adjustable UV emitters are arranged radially along a circumference of the housing, and
the heads of the adjustable UV emitters project outward from the housing, and each of the heads retains a UV LED.

11. The apparatus of claim 9 wherein:
the embedded UV emitters and the adjustable UV emitters are configured to emit UV light at a wavelength of (222) nanometers.

12. The apparatus of claim 9 wherein:
the rotational couplings comprise ball joints.

13. The apparatus of claim 9 wherein:
for each of the adjustable UV emitters, the rotational coupling defines a passage that houses wiring coupling a Light Emitting Diode (LED) of the adjustable UV emitter to a power supply of the adjustable UV emitter.

14. The apparatus of claim 9 further comprising:
a battery disposed within the housing that provides power to the disinfecting device.

15. The apparatus of claim 9 further comprising:
a controller that activates the embedded UV emitters and the adjustable UV emitters for a limited time period in response to receiving input from a user.

16. The apparatus of claim 9 wherein:
The disinfecting device is disposed within an enclosed space that comprises a portion of an aircraft, and the disinfecting device is affixed to the aircraft.

17. A method for disinfecting an enclosed space, the method comprising:
- attaching a disinfecting device having a plurality of adjustable UV emitters to a receiving surface of an enclosed space;
- providing for rotation of the adjustable UV emitters along multiple axes to enable each of the adjustable UV emitters to face a different portion of an object; and
- activating the disinfecting device to emit UV light from the adjustable UV emitters, wherein each of the adjustable UV emitters includes a corresponding power supply, and wherein activating the disinfecting device comprises activating each corresponding power supply of each of the adjustable UV emitters.

18. The method of claim 17 wherein:
attaching the disinfecting device comprises coupling the disinfecting device with an electrical system of an aircraft.

19. The method of claim 17 wherein:
emitting UV light comprises emitting UV light at a wavelength of (222) nanometers.

20. The method of claim 17 wherein:
providing for rotation comprises manipulating ball joints of the adjustable UV emitters.

* * * * *